(12) United States Patent
Lowe, III

(10) Patent No.: US 6,710,071 B2
(45) Date of Patent: Mar. 23, 2004

(54) DIFLUOROMETHYLENE AROMATIC ETHERS AS INHIBITORS OF GLYCINE TRANSPORT

(75) Inventor: John Adams Lowe, III, Stonington, CT (US)

(73) Assignee: Pfizer Inc, New York, NY (US)

(*) Notice: Subject to any disclaimer, the term of this patent is extended or adjusted under 35 U.S.C. 154(b) by 69 days.

(21) Appl. No.: 10/219,572

(22) Filed: Aug. 15, 2002

(65) Prior Publication Data

US 2003/0045569 A1 Mar. 6, 2003

Related U.S. Application Data

(60) Provisional application No. 60/325,752, filed on Aug. 16, 2001.

(51) Int. Cl.[7] .................... A61K 31/198; A61K 31/381; C07D 333/66
(52) U.S. Cl. .................. 514/438; 514/471; 514/519; 514/562; 514/563; 514/567; 514/443; 549/55; 549/494; 558/414; 562/426; 562/443
(58) Field of Search .................... 514/354, 438, 514/471, 519, 562, 563, 567; 549/55, 443, 474; 562/426, 443; 558/414

(56) References Cited

FOREIGN PATENT DOCUMENTS

| WO | WO9745115 | 12/1997 |
|---|---|---|
| WO | WO 97/45115 * | 12/1997 .......... A61K/31/24 |

* cited by examiner

*Primary Examiner*—Samuel Barts
*Assistant Examiner*—Ganapathy Krishnan
(74) *Attorney, Agent, or Firm*—Peter C. Richardson; Paul H. Ginsburg; Jolene W. Appleman

(57) ABSTRACT

This invention relates to a series of difluoromethylene aromatic ethers of the formula

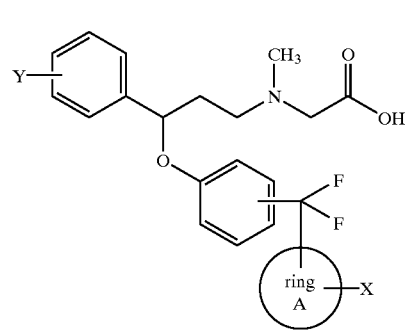

I wherein ring A and X and Y are defined as in the specification, that exhibit activity as glycine transport inhibitors, their pharmaceutically acceptable salts, pharmaceutical compositions containing them, and their use for the enhancement of cognition and the treatment of the positive and negative symptoms of schizophrenia and other psychoses in mammals, including humans.

17 Claims, No Drawings

DIFLUOROMETHYLENE AROMATIC ETHERS AS INHIBITORS OF GLYCINE TRANSPORT

This application claims the benefit of Provisional Patent Application Serial No. 60/325,752, filed Aug. 16, 2001.

BACKGROUND

The present invention relates to difluoromethylene aromatic ethers containing a pendant amino acid side chain and to pharmaceutical compositions containing them and to their use in the treatment of central nervous system disorders, cognitive disorders, schizophrenia, dementia and other disorders in mammals, including humans. These compounds exhibit activity as inhibitors of the glycine type-1 transporter.

Pharmacological treatment for schizophrenia has traditionally involved blockade of the dopamine system, which is thought to be responsible for its positive symptoms. Such treatment, however, ignores the negative and cognitive aspects of the disease. Another neurotransmitter system believed to play a role in schizophrenia is the glutamate system, the major excitatory transmitter system in the brain. This hypothesis is based on the observation that blockade of the glutamate system by compounds such as PCP ("angel dust") can replicate many of the symptoms of schizophrenia, including its positive, negative, and cognitive aspects. If schizophrenia involves a deficit of glutamatergic transmission, augmentation of the glutamate system, and specifically the NMDA receptor, may be beneficial. While glutamate is the principle agonist at NMDA receptors, glycine is required as a co-agonist to set the "tone" of the receptor for its response to glutamate. Enhancing this "tone" by increasing the effect of glycine would augment NMDA neurotransmission, and provide potential benefit in the treatment of schizophrenia.

A specific mechanism for augmenting the glycinergic "tone" of the NMDA receptor was disclosed recently by Bergeron, et al. (*Proc. Natl. Acad. Sci. USA*, 95, 15730, (1998)). This group showed that a specific and potent inhibitor of the glycine type-1 transporter (GlyT1) responsible for removing glycine from the synapse at the NMDA receptor, termed NFPS (WO 97/45115), can enhance NMDA receptor function. For example, NFPS increased the post synaptic current driven by the NMDA receptor, an effect blocked by both a specific NMDA-site antagonist and a glycine-site antagonist. Even though glycine levels in the brain are high relative to the amount required to act as an NMDA receptor co-agonist, this work shows that GlyT1 removes glycine efficiently at the synapse, and that inhibition of GlyT1 can augment NMDA receptor function. The authors establish the feasibility of using a GlyT1 inhibitor as a treatment for schizophrenia through its augmentation of glutamatergic neurotransmission.

SUMMARY OF THE INVENTION

The present invention relates to a series of compounds of the formula:

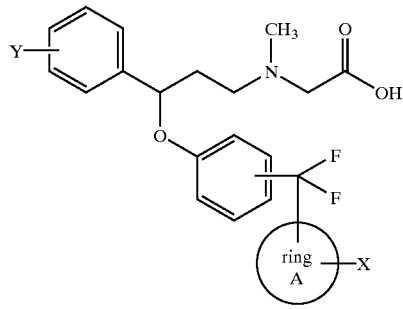

I wherein ring A is phenyl, naphthyl, benzothienyl, benzofuranyl, or thienyl; or ring A is a monocyclic aryl or heteroaryl ring containing from zero to four heteroatoms and not containing any adjacent ring oxygen atoms; or ring A is a bicyclic aryl or heteroaryl ring containing from zero to five heteroatoms and not containing any adjacent ring oxygen atoms; and X and Y are each, independently, $(C_1-C_6)$ alkyl optionally substituted with from one to seven fluorine atoms; $(C_1-C_6)$ alkoxy optionally substituted with from one to seven fluorine atoms, wherein the number of fluorine substituents on the foregoing $(C_1-C_6)$ alkyl and $(C_1-C_6)$ alkoxy groups cannot exceed the number of positions in such groups that are available for substitution; carboxy; carbo-$(C_1-C_6)$ alkoxy; carboxamido; $(C_1-C_6)$alkyl-thio; sulfoxyl; sulfonyl; halo; nitro; cyano; amino; $(C_1-C_6)$ alkylamino and di[$(C_1-C_6)$ alkyl]amino;

and the pharmaceutically acceptable salts of such compounds.

In a preferred embodiment of this invention, ring A is selected from phenyl, naphthyl benzofuranyl, benzothienyl, indanyl, tetrahydronaphthyl, dihydrobenzofuranyl, and dihydrobenzothiophenyl. In another preferred embodiment of this invention, X is para-trifluoromethyl, para-methyl or para-chloro.

The present invention also relates to a compound having the formula:

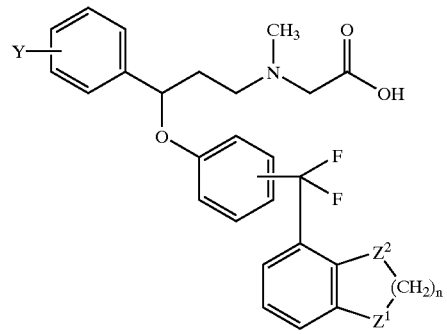

IA wherein Y is $(C_1-C_6)$alkyl optionally substituted with from one to seven fluorine atoms; $(C_1-C_6)$alkoxy optionally substituted with from one to seven fluorine atoms, wherein the number of fluorine substituents on the foregoing $(C_1-C_6)$ alkyl and $(C_1-C_6)$ alkoxy groups can not exceed the number of positions in such groups that are available for substitution; carboxy; carbo-$(C_1-C_6)$alkoxy; carboxamido; $(C_1-C_6)$ alkyl-thio; sulfoxyl; sulfonyl; halo; nitro; cyano; amino; $(C_1-C_6)$ alkylamino and di{$(C_1-C_6)$alkyl}amino;

wherein $Z^1$ and $Z^2$ are independently selected from O, NH, N-$(C_1-C_5$ alkyl), and S; and n is an integer from 1 to about 3;

or a pharmaceutically acceptable salt thereof.
Specific compounds of the invention include:
({3-[3-(Difluoro-(phenyl)methyl)phenoxy]-3-phenylpropyl}methylamino)acetic acid;
({3-[3-(Difluoro-(4-methoxyphenyl)methyl)phenoxy]-3-phenylpropyl}methylamino)acetic acid;
({3-[3-(Difluoro-(4-methylphenyl)methyl)phenoxyl]-3-phenylpropyl}methylamino)acetic acid;
({3-[3-(Difluoro-(4-chlorophenyl)methyl)phenoxy]-3-phenylpropyl}methylamino)acetic acid;
({3-[3-(Difluoro-(2,4-difluoroorophenyl)methyl)phenoxy]-3-phenylpropyl}methylamino)acetic acid;
({3-[3-(Difluoro-(benzo[b]furan-5-yl)methyl)phenoxy]-3-phenylpropyl}methylamino)acetic acid;
({3-[4-(Difluoro-(phenyl)methyl)phenoxy]-3-phenylpropyl}methylamino)acetic acid;
({3-[4-(Difluoro-(4-methoxyphenyl)methyl)phenoxy]-3-phenylpropyl}methylamino)acetic acid;
({3-[4-(Difluoro-(4-methylphenyl)methyl)phenoxy]-3-phenylpropyl}methylamino)acetic acid;
({3-[4-(Difluoro-(4-chlorophenyl)methyl)phenoxy]-3-phenylpropyl}methylamino)acetic acid;
({3-[4-(Difluoro-(phenyl)methyl)phenoxy]-3-phenylpropyl}methylamino)acetic acid; ({3-[4-(Difluoro-(benzo[b]furan-5-yl)methyl)phenoxy]-3-phenylpropyl}methylamino)acetic acid;
({3-(4-Fluoro)phenyl-3-[4-(difluoro-(benzo[b]furan-5-yl)methyl)phenoxy]propyl}methylamino)acetic acid;
({3-(2,4-Difluoro)phenyl-3-[4-(difluoro-(benzo[b]furan-5-yl)methyl)phenoxy]propyl}methylamino)acetic acid;
({3-[4-(Difluoro-(4-methylphenyl)methyl)phenoxy]-3-phenylpropyl}methylamino)acetic acid; and
({3-[4-(Difluoro-(4-chlorophenyl)methyl)phenoxy]-3-phenylpropyl}methylamino)acetic acid;
Other embodiments of the invention include:
({3-(4-Fluorophenyl)-3-[4-(difluoro-(5,6,7,8-tetrahydronaphthalen-1-yl)methyl)phenoxy]propyl}-methylamino)acetic acid;
({3-[4-(Difluoro-(2,4-dimethylphenyl)methyl)phenoxy]-3-(4-fluorophenyl)propyl}methylamino)acetic acid;
({3-(4-Fluorophenyl)-3-[4-(difluoro-(2,4,6-trimethylphenyl)methyl)phenoxy]propyl}methylamino)acetic acid;
({3-[4-(Difluoro-(5,6,7,8-tetrahydronaphthalen-1-yl)methyl)phenoxy]-3-phenylpropyl}methylamino)acetic acid;
({3-[4-(Difluoro-(2,4-dimethylphenyl)methyl)phenoxy]-3-phenylpropyl}methylamino)acetic acid;
({3-[4-(Difluoro-(4-cyclohexylphenyl)methyl)phenoxy]-3-(4-fluorophenyl)propyl}methylamino)acetic acid;
({3-[4-(Difluoro-(4-cyclopentylphenyl)methyl)phenoxy]-3-(4-fluorophenyl)propyl}methylamino)acetic acid;
({3-[4-(Difluoro-(4-cyclohexylphenyl)methyl)phenoxy]-3-phenylpropyl}methylamino)acetic acid;
({3-[4-(Difluoro-(4-cyclopentylphenyl)methyl)phenoxy]-3-phenylpropyl}methylamino)acetic acid;
({3-[4-(Difluoro-(2,3-dihydrobenzo[1,4]dioxin-5-yl)methyl)phenoxy]-3-(4-fluorophenyl)propyl}-methylamino)acetic acid;
({3-[4-(Difluoro-(2,3-dihydrobenzo[1,4]dioxin-5-yl)methyl)phenoxy]-3-phenylpropyl}methylamino)acetic acid;
({3-[4-(Difluoro-(2,3-dihydrobenzofuran-7-yl)methyl)phenoxy]-3-(4-fluorophenyl)-propyl}methylamino)acetic acid;
({3-[4-(Difluoro-(2,3-Dihydrobenzofuran-7-yl)methyl)phenoxy]-3-phenylpropyl}methylamino)acetic acid;
({3-[4-(Difluoro-(benzofuran-4-yl)methyl)phenoxy]-3-(4-fluorophenyl)-propyl}methylamino)acetic acid;
({3-[4-(Difluoro-(2,3-dihydrobenzofuran-4-yl)methyl)phenoxy]-3-phenylpropyl}methylamino)acetic acid;
({3-[4-(Difluoro-(2,3-dihydrobenzofuran-4-yl)methyl)phenoxy]-3-(4-fluorophenyl)propyl}methylamino)acetic acid;
({3-[4-(Difluoro-(3,5-bis(trifluoromethyl)phenyl)methyl)phenoxy]-3-(4-fluorophenyl)propyl}methylamino)acetic acid;
({3-(4-Fluorophenyl)-3-[4-(difluoro-(4-(trifluoromethoxy)phenyl)methyl)phenoxy]propyl}methylamino)acetic acid;
(Methyl-{3-phenyl-3-[4-(difluoro-(4-trifluoromethoxyphenyl)methyl)phenoxy]propyl}amino)acetic acid;
({3-[4-(Difluoro-(benzo[1,3]dioxol-5-yl)methyl)phenoxy]-3-(4-fluorophenyl)propyl}methylamino)acetic acid;
({3-[4-(Difluoro-(benzo[1,3]dioxol-5-yl)methyl)phenoxy]-3-phenylpropyl}methylamino)acetic acid;
({3-[4-(Difluoro-(3-methoxyphenyl)methyl)phenoxy]-3-phenylpropyl}methylamino)acetic acid;
({3-(4-Fluorophenyl)-3-[4-(difluoro-(3-methoxyphenyl)methyl)phenoxy]propyl}methylamino)acetic acid;
(Methyl-{3-phenyl-3-[4-(difluoro-(3-trifluoromethoxyphenyl)methyl)phenoxy]propyl}amino)acetic acid;
({3-(4-Fluorophenyl)-3-[4-(difluoro-(3-trifluoromethoxyphenyl)methyl)phenoxy]propyl}methylamino)acetic acid;
({3-[4-(Difluoro-(2-methoxyphenyl)methyl)phenoxy]-3-phenylpropyl}methylamino)acetic acid;
({3-(4-Fluorophenyl)-3-[4-(difluoro-(2-methoxyphenyl)methyl)phenoxy]propyl}methylamino)acetic acid;
({3-[4-(Difluoro-(3,4-dimethoxyphenyl)methyl)phenoxy]-3-phenylpropyl}methylamino)acetic acid;
({3-[4-(Difluoro-(3,4-dimethoxyphenyl)methyl)phenoxy]-3-(4-fluorophenyl)propyl}methylamino)acetic acid;
(Methyl-{3-(4-trifluoromethyl)phenyl-3-[4-(difluoro-(3-methoxyphenyl)methyl)-phenoxy]propyl}amino)acetic acid;
(Methyl-{3-phenyl-3-[4-(difluoro-(3-trifluoromethylphenyl)methyl)phenoxy]propyl}amino)acetic acid;
(Methyl-{3-phenyl-3-[4-(difluoro-(p-tolyl)methyl)phenoxy]propyl}amino)acetic acid;
(Methyl-3-{[4-(difluoro-(naphthalen-2-yl)methyl)phenoxy]-3-phenylpropyl}amino)acetic acid;
({3-[4-(Difluoro-(4-isopropylphenyl)methyl)phenoxy]-3-phenylpropyl}methylamino)acetic acid;
({3-[4-(Difluoro-(4-t-butylphenyl)methyl)phenoxy]-3-phenylpropyl}methylamino)acetic acid;
(Methyl-{3-phenyl-3-[4-(difluoro-(4-trifluoromethylphenyl)methyl)phenoxy]propyl}amino)acetic;
(Methyl-{3-phenyl-3-[4-(difluoro-(5,6,7,8-tetrahydronaphthalen-2-yl)methyl)phenoxy]propyl}amino)acetic acid;

(Methyl-{3-[4-(difluoro-(benzo[b]thien-5-yl)methyl)
phenoxy]-3-phenylpropyl}amino)acetic acid; and (Methyl-{3-(4-fluorophenyl)-{3-[4-(difluoro-(benzo[b]
thien-5-yl)methyl)phenoxy]propyl}amino)acetic acid.

This invention also relates to a method of treating a disorder or condition selected from psychosis, schizophrenia, conduct disorder, disruptive behavior disorder, bipolar disorder, psychotic episodes of anxiety, anxiety associated with psychosis, psychotic mood disorders such as severe major depressive disorder; mood disorders associated with psychotic disorders such as acute mania or depression associated with bipolar disorder and mood disorders associated with schizophrenia, behavioral manifestations of mental retardation, conduct disorder and autistic disorder; movement disorders such as Tourette's syndrome, akinetic-rigid syndrome, movement disorders associated with Parkinson's disease, tardive dyskinesia and other drug induced and neurodegeneration based dyskinesias; attention deficit hyperactivity disorder; cognitive disorders such as dementias (including age related dementia, and senile dementia of the Alzheimer's type) and memory disorders in a mammal, including a human, comprising administering to a mammal in need of such treatment an amount of a compound of the formula I, or a pharmaceutically acceptable salt thereof, that is effective in treating such condition or disorder.

This invention also relates to a pharmaceutical composition for treating a disorder or condition selected from psychosis, schizophrenia, conduct disorder, disruptive behavior disorder, bipolar disorder, psychotic episodes of anxiety, anxiety associated with psychosis, psychotic mood disorders such as severe major depressive disorder; mood disorders associated with psychotic disorders such as acute mania or depression associated with bipolar disorder and mood disorders associated with schizophrenia, behavioral manifestations of mental retardation, conduct disorder and autistic disorder; movement disorders such as Tourette's syndrome, akinetic-rigid syndrome, movement disorders associated with Parkinson's disease, tardive dyskinesia and other drug induced and neurodegeneration based dyskinesias; attention deficit hyperactivity disorder; cognitive disorders such as dementias (including age related dementia and senile dementia of the Alzheimer's type) and memory disorders in a mammal, including a human, comprising a compound of the formula I, or a pharmaceutically acceptable salt thereof, in an amount that is effective for treating such disorder or condition.

This invention also relates to a method of treating a disorder or condition selected from psychosis, schizophrenia, conduct disorder, disruptive behavior disorder, bipolar disorder, psychotic episodes of anxiety, anxiety associated with psychosis, psychotic mood disorders such as severe major depressive disorder; mood disorders associated with psychotic disorders such as acute mania or depression associated with bipolar disorder and mood disorders associated with schizophrenia, behavioral manifestations of mental retardation, conduct disorder and autistic disorder; movement disorders such as Tourette's syndrome, akinetic-rigid syndrome, movement disorders associated with Parkinson's disease, tardive dyskinesia and other drug induced and neurodegeneration based dyskinesias; attention deficit hyperactivity disorder; cognitive disorders such as dementias (including age related dementia and senile dementia of the Alzheimer's type) and memory disorders in a mammal, including a human, comprising administering to a mammal in need of such treatment a glycine transport-inhibiting amount of a compound of the formula I, or a pharmaceutically acceptable salt thereof.

This invention also relates to a pharmaceutical composition for treating a disorder or condition selected from psychosis, schizophrenia, conduct disorder, disruptive behavior disorder, bipolar disorder, psychotic episodes of anxiety, anxiety associated with psychosis, psychotic mood disorders such as severe major depressive disorder; mood disorders associated with psychotic disorders such as acute mania or depression associated with bipolar disorder and mood disorders associated with schizophrenia, behavioral manifestations of mental retardation, conduct disorder and autistic disorder; movement disorders such as Tourette's syndrome, akinetic-rigid syndrome, movement disorders associated with Parkinson's disease, tardive dyskinesia and other drug induced and neurodegeneration based dyskinesias; attention deficit hyperactivity disorder; cognitive disorders such as dementias (including age related dementia and senile dementia of the Alzheimer's type) and memory disorders in a mammal, including a human, comprising a compound of the formula I, or a pharmaceutically acceptable salt thereof, in a glycine transport-inhibiting amount.

The term "alkyl", as used herein, unless otherwise indicated, includes saturated monovalent hydrocarbon radicals having straight, branched or cyclic moieties or combinations thereof. Examples of "alkyl" groups include, but are not limited to, methyl, ethyl, propyl, isopropyl, butyl, isobutyl, sec-butyl, tert-butyl, pentyl, hexyl, heptyl, 3-ethylbutyl, cyclopropyl, cyclobutyl, cyclopentyl, cyclohexyl, cycloheptyl, norbornyl, and the like.

The term "halo", as used herein, means chloro, fluoro, iodo or bromo.

The term "alkoxy", as used herein, means "alkyl-O-", wherein "alkyl" is defined as above.

The term "treating", as used herein, refers to reversing, alleviating, inhibiting the progress of, or preventing the disorder or condition to which such term applies, or one or more symptoms of such condition or disorder. The term "treatment", as used herein, refers to the act of treating, as "treating" is defined immediately above.

The compounds of formula I may have optical centers and therefore may occur in different enantiomeric configurations. Formula I, as depicted above, includes all enantiomers, diastereomers, and other stereoisomers of the compounds depicted in structural formula I, as well as racemic and other mixtures thereof. Individual isomers can be obtained by known methods, such as optical resolution, optically selective reaction, or chromatographic separation in the preparation of the final product or its intermediate.

The present invention also includes isotopically labelled compounds, which are identical to those recited in formula I, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, phosphorous, sulfur, fluorine and chlorine, such as $^{2}H$, $^{3}H$, $^{13}C$, $^{11}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically labelled compounds of the present invention, for example those into which radioactive isotopes such as $^{3}H$ and $^{14}C$ are incorporated, are useful in drug and/or substrate tissue distribution assays. Tritium and $^{14}C$ isotopes are particularly preferred for their ease of preparation and detectability. Further, substitution with heavier isotopes such as deuterium can afford certain therapeutic advantages resulting from greater metabolic stability, for example increased in vivo half-life or reduced dosage requirements and, hence, may be preferred in some circumstances. Isotopically labelled compounds of formula I of this invention and prodrugs thereof can generally be prepared by carrying out the procedures disclosed in the Scheme and/or in the Examples and Preparations below, by substituting a readily available isotopically labelled reagent for a non-isotopically labelled reagent.

DETAILED DESCRIPTION OF THE INVENTION

The compounds of the formula I of this invention may be prepared as described in the following reaction schemes.

Unless otherwise indicated, in the reaction schemes and discussion that follow, X and Y are defined as above.

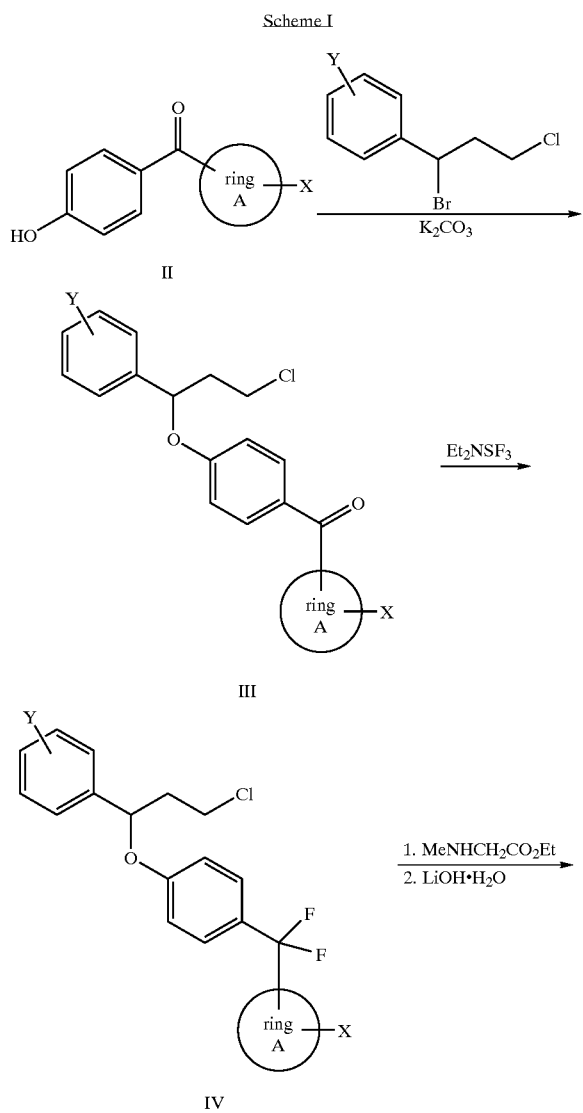
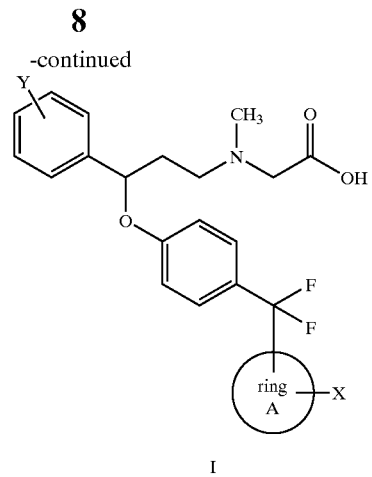

Scheme I illustrates methods of preparing compounds of the formula I wherein ring A is phenyl. Methods analogous to these can be used to prepare compounds of the formula I wherein ring A is other than phenyl. Such methods will be understood by those of skill in the art.

Referring to Scheme I, a compound of formula II is reacted with optionally aryl-substituted 3-chloro-1-bromo-1-phenylpropane in the presence of an alkali metal or alkaline earth metal carbonate or bicarbonate to form the corresponding aromatic ketoether of formula III. This reaction is typically conducted in a dipolar solvent such as acetone, 2-butanone or methylisobutyl ketone, at a temperature from about 30° C. to about 120° C., preferably at the reflux temperature of the selected solvent. The resulting ketoether is then converted to the corresponding gem-dihalo ether compound of formula IV by treatment with a halogenating agent, such as diethylaminosulfur trifluoride, at a temperature from about 60° C. to about 80° C., preferably at about 70–75° C.

The gem-dihalo ether compound of formula IV is then treated with an aminoacetic ester such as N-methyl glycine ethyl ester (sarcosine ethyl ester) in the presence of an organic base such as diisopropylethylamine or diethylamine. This reaction is typically conducted in a reaction-inert solvent such as N-methylpyrrolidinone or dimethyl formamide, at a temperature from about room temperature to about 150° C., preferably at about 90° C. Then, the resulting ester is hydrolyzed using an alkali metal carbonate or bicarbonate or an alkali metal hydroxide, preferably an alkali metal hydroxide, such as lithium hydroxide, in water, a mixture of water, an alcohol containing one to four carbons and/or an ethereal solvent such as tetrahydrofuran to form the corresponding gem-dihalo aromatic ether carboxylic acid of formula I. The hydrolysis reaction can be carried out in situ or after isolating the ester from the alkylation reaction. In either case, the hydrolysis is carried out using the same or similar solvent as that used in the alkylation reaction and is carried out under the same or similar conditions.

As shown in Scheme II, the phenolic alcohol compound of formula V is treated with optionally aryl-substituted 3-chloro-1-bromo-1-phenylpropane in the presence of an alkali metal or alkaline earth metal carbonate or bicarbonate so as to form a haloalkylphenoxy aryl ester of formula VI. This reaction is typically conducted in a dipolar solvent such as acetone, 2-butanone or methylisobutyl ketone, at a temperature from about 30° C. to about 120° C., preferably at the reflux temperature of the selected solvent. The resulting a haloalkylphenoxy aryl ester of formula VI is hydrolyzed using an alkali metal carbonate or bicarbonate or an alkali metal hydroxide, preferably an alkali metal hydroxide, such as lithium hydroxide, in water, a mixture of water, an alcohol containing one to four carbons and/or an ethereal solvent such as tetrahydrofuran to form the corresponding haloakylphenoxy aryl carboxylic acid. Formation of the haloakylphenoxy aryl acid halide of formula VII is carried out by methods know to workers in the art. In particular, the carboxylic acid may be treated with a thionyl halide such as thionyl chloride or bromide in a reaction-inert solvent such a dichloromethane or dichloroethane at a temperature from about 25° C. to about 110° C., preferably at the reflux temperature of the selected solvent.

The haloakylphenoxy aryl acid halide of formula VII may be treated with a substituted aromatic boronic acid such as p-toly boronic acid in the presence of (a) a cesium salt such as cesium carbonate and (b) a palladium catalyst such as tetrakis(triphenylphosphine)palladium, so as to form the ketoether of formula III. The reaction is preferably conducted in a reaction-inert solvent such as toluene or xylene at a temperature from about 80° C. to about 140° C., preferably at about 100° C.

The ketoether of formula III is then converted to the corresponding gem-dihalo ether compound of formula IV as described above regarding the similar process in Scheme I.

The gem-dihalo ether compound of formula IV is then treated with an aminoacetic ester such as N-methyl glycine ethyl ester (sarcosine ethyl ester) as described above regarding the similar process in Scheme I.

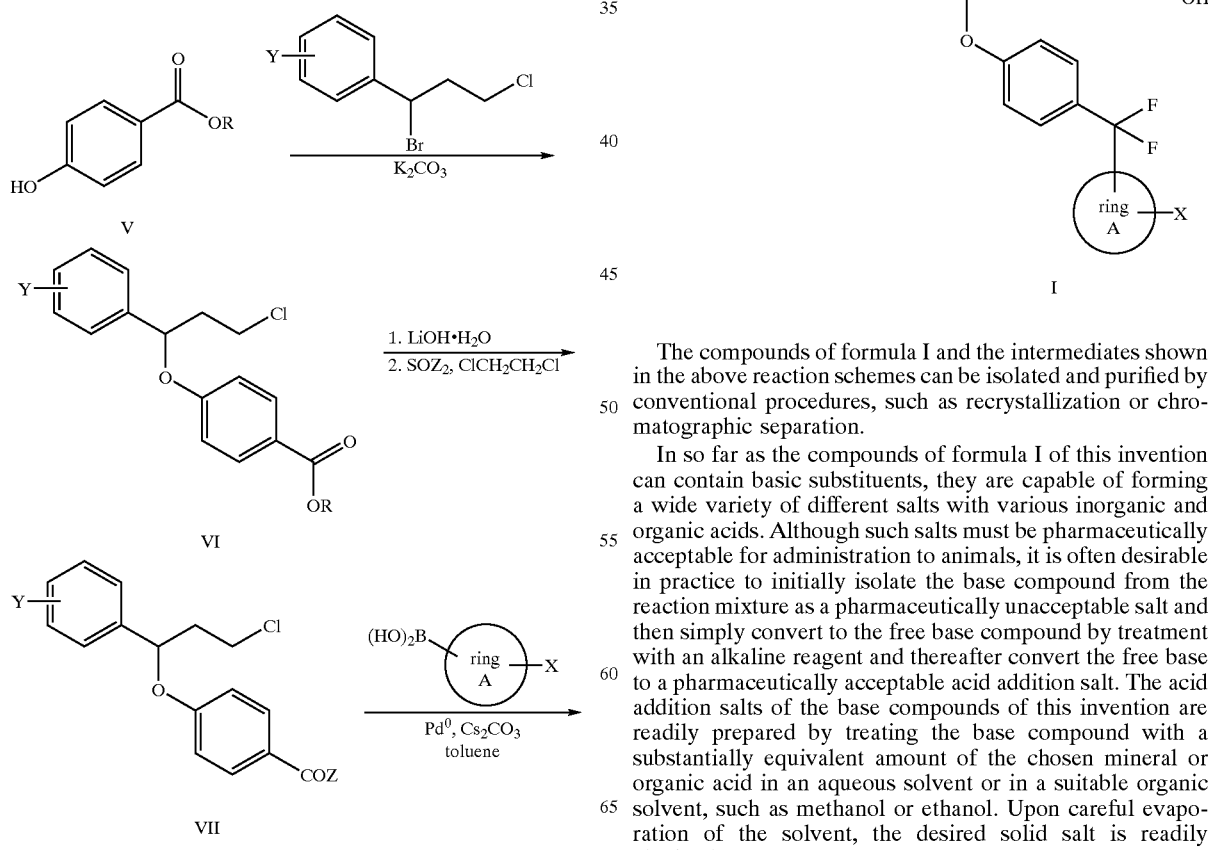

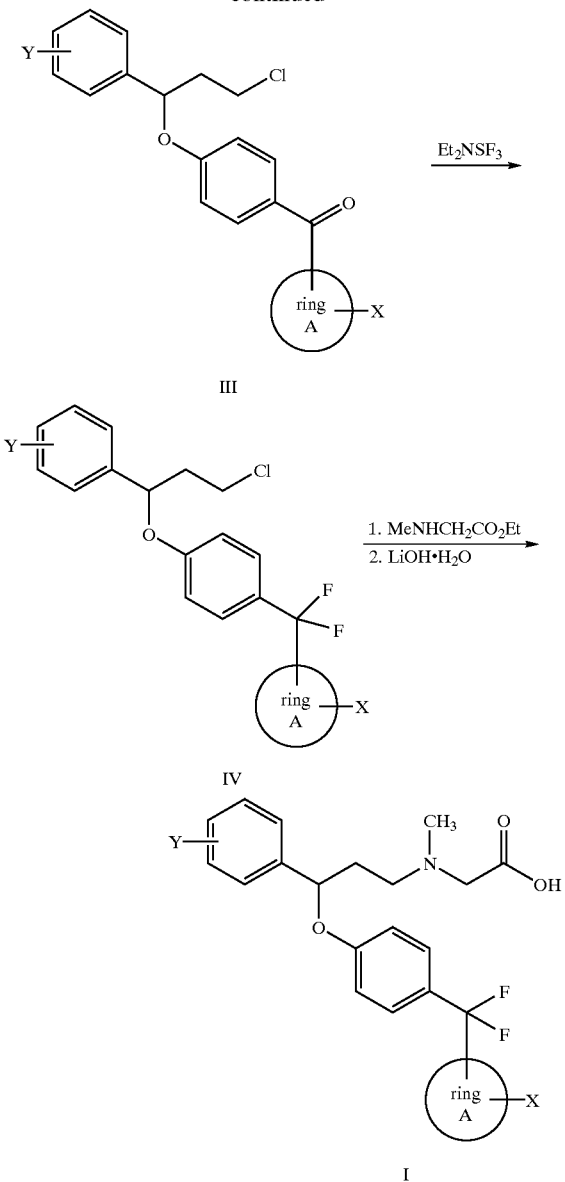

The compounds of formula I and the intermediates shown in the above reaction schemes can be isolated and purified by conventional procedures, such as recrystallization or chromatographic separation.

In so far as the compounds of formula I of this invention can contain basic substituents, they are capable of forming a wide variety of different salts with various inorganic and organic acids. Although such salts must be pharmaceutically acceptable for administration to animals, it is often desirable in practice to initially isolate the base compound from the reaction mixture as a pharmaceutically unacceptable salt and then simply convert to the free base compound by treatment with an alkaline reagent and thereafter convert the free base to a pharmaceutically acceptable acid addition salt. The acid addition salts of the base compounds of this invention are readily prepared by treating the base compound with a substantially equivalent amount of the chosen mineral or organic acid in an aqueous solvent or in a suitable organic solvent, such as methanol or ethanol. Upon careful evaporation of the solvent, the desired solid salt is readily obtained.

The acids which are used to prepare the pharmaceutically acceptable acid addition salts of the aforementioned base compounds of this invention are those which form non-toxic acid addition salts, i.e., salts containing pharmaceutically acceptable anions, such as the hydrochloride, hydrobromide, hydroiodide, nitrate, sulfate or bisulfate, phosphate or acid phosphate, acetate, lactate, citrate or acid citrate, tartrate or bi-tartrate, succinate, maleate, fumarate, gluconate, saccharate, benzoate, methanesulfonate, ethanesulfonate, benzenesulfonate, ptoluenesulfonate and pamoate (i.e., 1,1'-methylene-bis-(2-hydroxy-3-naphthoate))salts.

All compounds of the invention have an acidic group and are capable of forming base salts with various pharmaceutically acceptable cations. Examples of such salts include the alkali metal or alkaline-earth metal salts and, particularly, the sodium and potassium salts. These salts are all prepared by conventional techniques.

The chemical bases which are used as reagents to prepare the pharmaceutically acceptable base salts of this invention are those which form non-toxic base salts with the herein described acidic derivatives. These particular non-toxic base salts include those derived form such pharmaceutically acceptable cations as sodium, potassium, calcium and magnesium, etc. These salts can easily be prepared by treating the aforementioned acidic compounds with an aqueous solution containing the desired pharmaceutically acceptable cation, and then evaporating the resulting solution to dryness, preferably under reduced pressure. Alternatively, they may also be prepared by mixing lower alkanoic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum production of yields of the desired final product.

The compounds of the present invention exhibit significant glycine transport inhibiting activity and therefore are of value in the treatment of a wide variety of clinical conditions that are characterized by the deficit of glutamergic neurotransmission in mammalian subjects, especially humans. Such conditions include the positive and negative symptoms of schizophrenia and other psychoses, and cognitive deficits.

The compounds of formula I of this invention can be administered via the oral, parenteral (such as subcutaneous, intravenous, intramuscular, intrasternal and infusion techniques), rectal, intranasal or topical routes to mammals. In general, these compounds are most desirably administered to humans in doses ranging from about 1 mg to about 2000 mg per day, although variations will necessarily occur depending upon the weight and condition of the subject being treated and the particular route of administration chosen. However, a dosage level that is in the range of from about 0.1 mg to about 20 mg per kg of body weight per day is most desirably employed. Nevertheless, variations may still occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effects provided that such higher dose levels are first divided into several small doses for administration throughout the day.

The compounds of the present invention may be administered alone or in combination with pharmaceutically acceptable carriers or diluents by either of the above routes previously indicated, and such administration can be carried out in single or multiple doses. More particularly, the novel therapeutic agents of the invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various nontoxic organic solvents, etc. Moreover, oral pharmaceutical compositions can be suitably sweetened and/or flavored. In general, the therapeutically effective compounds of this invention are present in such dosage forms at concentration levels ranging about 5.0% to about 70% by weight.

For oral administration, tablets containing various excipients such as microcrystalline cellulose, sodium citrate, calcium carbonate, dicalcium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatine capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intramuscular and subcutaneous injection purposes. The preparation of all these solutions under sterile conditions is readily accomplished by standard pharmaceutical techniques well-known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

The compounds of the present invention are assayed for their activity in inhibiting glycine reuptake in synaptosomes by first preparing synaptosomes and then measuring neurotransmitter reuptake activity as follows:

Male Sprague Dawley rats are decapitated and the brains removed. The whole brains are dissected out and placed in ice cold sucrose buffer; 1 gram in 20 mis (320 mM sucrose containing 1 mg/ml glucose, 0.1 mM EDTA and brought up to pH 7.4 with Tris base). The tissue is homogenized in a glass homogenizing tube with a Teflon™ pestle at 350 RPMS using a Potters homogenizer. The homogenate is centrifuged at 1000×g for 10 min at 4° C. The resulting supernatant is recentrifuged at 17,000×g for 20 min at 4° C. The final pellet is resuspended in an appropriate volume of sucrose buffer containing 5 mM alanine, to yield less than 10% uptake.

The uptake assays are conducted in 96 well matrix plates. Each well contains 25 μL of solvent, inhibitor or 10 mM glycine for nonspecific uptake, 200 μL of [$^3$H]-glycine (40 nM final), made up in modified Krebs containing 5 mM alanine and glucose (1 mg/ml) and 25 μL of synaptosomes. The plates are then incubated at room temperature for the 15 min. The incubation is terminated by filtration through GF/B filters, using a 96 well Brandel Cell Harvester. The filters are washed with modified Krebs buffer and counted in a liquid scintillation counter or in a LKB Beta Plate counter. Compounds of the invention analyzed by this assay have been found to have significant activity in inhibiting glycine reuptake in synaptosomes, having $IC_{50}$ values of no greater than 50 nM.

The present invention is illustrated by the following examples. However, it should be understood that the invention is not limited to the specific details of these examples. Melting points were taken with a Buchi micro melting point apparatus and uncorrected. Infrared Ray absorption spectra (IR) were measured by a Shimadzu infrared spectrometer (IR-470). $^1$H and $^{13}$C nuclear magnetic resonance spectra (NMR) were measured in $CDCl_3$ by a JEOL NMR spectrometer (JNM-GX270, 270 MHz for $^1$H, 67.5 MHz for $^{13}$C) unless otherwise indicated and peak positions are expressed in parts per million (ppm) downfield from tetramethylsilane. The peak shapes are denoted as follows: s, singlet; d, doublet; t, triplet; m, multiplet; br, broad.

EXAMPLE 1

({3-[4-(Difluoro(phenyl)methyl)phenoxy]-3-phenylpropyl}methylamino)acetic Acid

A. [4-(3-Chloro-1-phenylpropoxy)phenyl]phenylmethanone: To a 125 mL round-bottomed flask equipped with condenser and $N_2$ inlet were added 3.78 g (16.15 mmol) 3-chloro-1-bromo-1-phenylpropane, 3.52 g (17.76 mmol) 4-benzoylphenol, 4.46 g (32.3 mmol) potassium carbonate, and 27 mL methylisobutylketone. The reaction was refluxed 40 h, cooled, and poured into water. After extracting with ethyl acetate, the organic layer was washed with brine, dried over sodium sulfate, and evaporated. The residue was chromatographed on silica gel using ethyl acetate/hexane as eluant to afford 3.0 g (53%) of an oil.

$^1$H—NMR (δ, $CDCl_3$): 2.38 (AB, 2H), 3.73 (AB, 2H), 5.48 (dd, J=4,8, 1H), 6.92 (m, 2H), 7.2–7.8 (m, 12H).

$^{13}$C—NMR (δ, $CDCl_3$): 41.04, 41.13, 76.83, 115.28, 125.76, 126.53, 128.11, 128.41, 128.87, 129.61, 131.80, 133.54, 138.24, 139.96, 161.43, 195.34.

B. 3-Phenyl-3-[4-difluorobenzyl]-1-chloropropane: To a 125 mL round-bottomed flask equipped with condenser and $N_2$ inlet were added 1.04 g (2.97 mmol) [4-(3-chloro-1-phenylpropoxy)phenyl]phenylmethanone and 5.88 mL (44.5 mmol) diethylaminosulfur trifluoride. The reaction was heated at 70–75° C. (higher temperatures result in extensive decomposition of starting material, lower temperatures in a very slow reaction) for 40 h and cooled. The reaction was adsorbed onto silica gel and chromatographed on silica gel using hexane/ethyl acetate as eluant to afford 236 mg (21%) of an oil.

$^1$H—NMR (δ, $CDCl_3$): 2.2 and 2.5 (multiplets, 2H), 3.6 and 3.8 (multiplets, 2H), 5.44 (m, 1H), 6.91 (m, 2H), 7.2–7.6 (m, 12H).

$^{13}$C—NMR (δ, $CDCl_3$): 41.46, 41.59, 77.08, 115.80, 121.08 (t, J=240), 126.10, 127.62, 127.67, 128.33, 128.58, 129.16, 130.54 (t, J=29), 137.98 (t, J=28), 140.64, 159.30.

C. {[3-(4-Difluorophenylmethylphenoxy)-3-phenylpropyl]methylamino}acetic Acid Ethyl Ester: To a 125 mL round-bottomed flask equipped with condenser and $N_2$ inlet were added 236 mg (0.633 mmol) 3-phenyl-3-[4-difluorobenzyl]-1-chloropropane, 194 mg (1.37 mmol) sarcosine ethyl ester hydrochloride, 0.331 mL (1.90 mmol) diisopropylethylamine, and 5 mL dry N-methylpyrrolidinone. The reaction was heated at 90–95° C. for 50 h, cooled, and poured into water. After extracting with ethyl acetate, the organic layer was washed with water (3 times) and brine, dried over sodium sulfate, and evaporated. The residue was chromatographed on silica gel using methylene chloride/methanol as eluant to afford 57 mg (20%) of an oil.

$^1$H—NMR (δ, $CDCl_3$): 1.205 (t, J=7, 3H), 1.9 and 2.2 (multiplets, 2H), 2.36 (s, 3H), 2.64 (m, 2H), 3.22 (s, 2H), 4.10 (q, J=7, 2H), 5.23 (m, 1H), 6.83 (m, 2H), 7.2–7.5 (m, 12H).

$^{13}$C—NMR (δ, $CDCl_3$): 14.46, 36.90, 42.48, 42.50, 53.37, 58.85, 60.65, 78.40, 115.70, 121.04 (t, J=239), 126.09, 127.44, 127.49, 127.54, 127.89, 128.47, 128.89, 129.90, 130.08 (t, J=28), 137.97 (t, J=28), 141.67, 159.55, 171.08.

MS (%): 454 (parent+1, 100).

D. ({3-[4-(Difluorophenylmethyl)-phenoxy]-3-phenylpropyl}methylamino)acetic Acid: To a 125 mL round-bottomed flask equipped with $N_2$ inlet were added the above ester dissolved in 5 mL tetrahydrofuran, followed by a solution of 40 mg lithium hydroxide hydrate in 5 mL water with sufficient methanol to give a solution. The reaction was stirred at room temperature for 1 h, evaporated, and taken up in 5 mL water. The pH was adjusted to 1 with 6N hydrochloric acid, and the aqueous layer extracted twice with methylene chloride. The organic layer was dried over sodium sulfate and evaporated to an oil, which solidified on standing under high vacuum to an amorphous solid, 51 mg (17%)

$^{13}$C—NMR (δ, CDCl3): 33.10, 41.94, 54.54, 56.40, 70.70, 115.90, 120.99 (t, J=239), 125.88, 125.94, 126.03, 127.53, 128.55, 129.20, 130.03, 130.64 (t, J=28), 137.69 (t, J=28), 139.83, 158.63, 166.85.

MS (%): 426 (parent+1) for APCl positive and 424 (parent−1) for APCl negative.

Anal. Calc'd. for $C_{25}H_{25}NO_3F_2HCl\cdot\frac{3}{4}H_2O$: C 63.16, H 5.83, N 2.95. Found: C 63.12, H 6.21, N 3.14.

EXAMPLE 2

({3-[4-(Difluoro-p-tolylmethyl)phenoxy]-3-phenylpropyl}methylamino)acetic Acid

A. 4-(3-Chloro-1-phenylpropoxy)benzoic Acid Methyl Ester: (Referring to Scheme 2)

Prepared as in Example 1A, using 4-(carbomethoxy)-phenol, in 71% yield, as an oil.

$^1$H—NMR (δ, $CDCl_3$): 2.37 (AB, 2H), 3.67 (AB, 2H), 3.815 (s, 3H), 5.44 (dd, J=5,8, 1H), 6.86 (m, 2H), 7.1–7.3 (m, 5H), 7.87 (m, 2H).

$^{13}$C—NMR (δ, $CDCl_3$): 41.33, 41.40, 52.03, 77.04, 115.66, 122.97, 126.06, 128.31, 128.36, 129.14, 131.70, 140.25, 161.81, 167.04.

This material was hydrolyzed as in Example 1C to provide 4-(3-chloro-1-phenyl-propoxy)-benzoic acid in 62% overall yield, which was used in the next step.

B. 4-(3-Chloro-1-phenylpropoxy)benzoyl Chloride: To a 125 mL round-bottomed flask equipped with condenser and $N_2$ inlet were added 1.0 g (3.44 mmol) 4-(3-chloro-1-phenyl-propoxy)benzoic acid, 20 mL 1,2-dichloroethane, and 0.3 mL (4.13 mmol) thionyl chloride. The solution was refluxed for 2 hours, evaporated, and the acid chloride used directly in the next step.

C. [4-(3-Chloro-1-phenylpropoxy)phenyl]-p-tolylmethanone: To a 125 mL round-bottomed flask equipped with condenser and $N_2$ inlet were added 1.06 g (3.44 mmol) 4-(3-chloro-1-phenylpropoxy)benzoyl chloride, 468 mg (3.44 mmol) p-tolyl boronic acid, 2.24 g (6.88 mmol) cesium carbonate, 40 mg (0.034 mmol) tetrakis(triphenylphosphine)palladium, and 25 mL dry toluene. The reaction was heated to 100° C. for 18 h, cooled, and poured into water. After extracting with ethyl acetate, the organic layer was washed with brine, dried over sodium sulfate, and evaporated. The residue was chromatographed on silica gel using ethyl acetate/hexane as eluant to afford 480 mg (38%) of an oil.

$^1$H—NMR (δ, $CDCl_3$): 2.35 (AB, 2H), 2.37 (s, 3H), 3.65 (AB, 2H), 5.48 (dd, J=5,8, 1H), 6.91 (m, 2H), 7.1–7.4 (m, 7H), 7.62 (m, 2H), 7.69 (m, 2H).

$^{13}$C—NMR (δ, $CDCl_3$): 21.82, 41.36, 41.44, 77.13, 115.56, 126.09, 128.40, 129.09, 129.18, 130.20, 132.51, 132.67, 135.62, 140.32, 142.81, 161.56, 195.33.

D. [4-(3-Chloro-1-phenylpropoxy)Phenyl]-p-tolyldifluoromethane: Prepared as in example 1B above, in 14% yield as an oil.

$^1$H—NMR (δ, $CDCl_3$): 2.2 and 2.4 (multiplets, 2H), 2.34 (s, 3H), 3.6 and 3.8 (multiplets, 2H), 5.39 (m, 1H), 6.85 (m, 2H), 7.2–7.4 (m, 11H).

$^{13}$C—NMR (δ, $CDCl_3$): 21.45, 41.41, 41.55, 77.02, 115.69, 121.16 (t, J=240), 125.95, 126.00, 126.05, 127.53, 127.59, 127.64, 128.26, 129.09, 129.16, 130.69 (t, J=28), 135.11 (t, J=28), 139.98, 140.62, 159.17.

E. ({3-[4-(Difluoro-p-tolylmethyl)phenoxy]-3-phenylpropyl}methylamino)acetic Acid Ethyl Ester: Prepared as in Example 1C in 27% yield as an oil.

$^1$H—NMR (δ, $CDCl_3$): 1.20 (t, J=7, 3H), 1.9 and 2.2 (multiplets, 2H), 2.32 (s, 3H), 2.36 (s, 3H), 2.65 (m, 2H), 3.22 (s, 2H), 4.11 (q, J=7, 2H), 5.22 (m, 1H), 6.81 (m, 2H), 7.1–7.4 (m, 11H).

$^{13}$C—NMR (δ, $CDCl_3$): 14.44, 36.82, 42.46, 53.36, 58.75, 60.70, 78.32, 115.64, 121.20 (t, J=240), 125.98, 126.07, 127.47, 127.89, 128.88, 129.11, 130.27 (t, J=29), 139.89 (t, J=29), 141.63, 159.45, 170.95.

MS (%): 468 (parent+1, 100).

E. ({3-[4-(Difluoro-p-tolylmethyl)phenoxy]-3-phenylpropyl}methylamino)acetic Acid: Prepared as in Example 1D in 18% overall yield, as an amorphous solid.

$^{13}$C—NMR (δ, CDCl3): 21.43, 33.99, 54.57, 56.5, 78.0, 115.57, 121.15 (t, J=240), 125.96, 126.05, 127.53, 128.48, 129.07, 129.18, 131.10 (t, J=29), 134.86 (t, J=29), 140.06, 158.56, 167.17.

MS (%): 440 (parent+1) and 438 (parent−1) at APCI negative

Anal. Calc'd for $C_{26}H_{27}NO_3F_2HCl\cdot\frac{2}{3}(H_2O)$: C 64.00, H 6.06, N 2.87. Found: C 63.86, H 6.66, N 3.42.

EXAMPLE 3

[(3-{4-[(4-Chlorophenyl)difluoromethyl]phenoxy}-3-phenylpropyl)methylamino]acetic Acid: Prepared as in Example 2 in 18% overall yield, as an amorphous solid.

$^{13}$C—NMR (δ, CDCl3): 38.92, 55.37, 56.0, 76.85, 115.93, 125.51, 126.00, 126.59, 127.13, 127.56, 128.63, 128.82, 129.26, 143.50, 164.06.

MS (%): 460 (parent+1) and 458 (parent−1) at APCI negative

EXAMPLE 4

(3-{4-[(2,4-Difluorophenyl)difluoromethyl]phenoxy}-3-phenylpropyl)methylamino]-acetic Acid: Prepared as in Example 2 in 26% overall yield, as an amorphous solid.

$^{13}$C—NMR (δ, $CDCl_3$): 33.00 and 33.41, 41.46 and 41.86, 54.46, 55.69 and 56.28, 105.29 (t, J=26), 111.30 (d, J=18), 115.95, 119.09 (t, J=242), 126.02, 127.19, 128.49, 128.69, 129.58 (t, J=29), 139.80, 158.90, 159.13 (dd, J=12, 250), 164.26 (dd, J=12, 253), 166.85.

MS (%): 462 (parent+1) and 460 (parent−1) at APCI negative

Anal. Calc'd for $C_{25}H_{23}NO_3F_4HCl\cdot H_2O$: C 58.20, H 5.08, N 2.71. Found: C 58.60, H 5.13, N 2.73.

EXAMPLE 5

[(3-{4-[(3-Trifluoromethylphenyl)difluoromethyl]phenoxy}-3-phenylpropyl)methyl-amino]acetic Acid: Prepared as in Example 2 in 16% overall yield, as an amorphous solid.

$^{13}$C—NMR (δ, $CDCl_3$): 32.95 and 33.40, 41.60, 54.57, 56.0, 116.10, 120.26 (t, J=254), 122.79, 126.01, 126.91, 127.45, 128.56, 129.23, 129.29, 129.51, 131.12 (q, J=36), 138.75 (t, J=29), 139.66, 158.87, 166.78.

MS (%): 494 (parent+1) and 492 (parent−1) at APCI negative

Anal. Calc'd for $C_{26}H_{24}NO_3F_5HCl$: C 58.93, H 4.76, N 2.64. Found: C 58.65, H 5.18, N 2.46.

EXAMPLE 6

[(3-{4-[(3,4-Difluorophenyl)difluoromethyl]phenoxy}-3-phenylpropyl)methylamino]-acetic Acid: Prepared as in Example 2 in 30% overall yield, as an amorphous solid.

$^{13}$C—NMR (δ, $CDCl_3$): 32.98 and 33.39, 41.54 and 41.925, 54.55, 55.77 and 56.42, 63.36, 115.768 (d, J=15), 116.05, 119.90 (t, J=274), 122.62, 126.02, 127.41, 128.54, 129.22, 134.73 (t, J=29), 139.74, 150.23 (dd, J=13, 249), 151.28 (dd, J=8, 252), 158.88, 166.89.

MS (%): 462 (parent+1) and 460 (parent−1) at APCI negative

Anal. Calc'd for $C_{25}H_{23}NO_3F_4HCl\cdot\frac{1}{2}(H_2O)$: C 59.23, H 4.97, N 2.76. Found: C 59.50, H 5.17, N 2.58.

EXAMPLE 7

[(3-{4-[(3-Chloro-4-fluorophenyl)difluoromethyl]phenoxy}-3-phenylpropyl)methyl-amino]acetic Acid: Prepared as in Example 2 in 25% overall yield, as an amorphous solid.

$^{13}$C—NMR (δ, $CDCl_3$): 32.97 and 33.37, 41.56 and 41.95, 54.55, 55.73 and 56.37, 78.0, 116.06, 116.85 (d, J=21), 119.94 (t, J=242), 121.58, 126.01, 126.26, 127.43, 128.56, 129.23, 131.32, 134.92 (t, J=29), 139.66, 157.75, 158.84, 160.26, 166.73.

MS (%): 478 (parent+1) and 476 (parent−1) at APCI negative

Anal. Calc'd for $C_{25}H_{23}NO_3F_3Cl\ HCl$: C 58.38, H 4.70, N 2.72. Found: C 58.39, H 4.88, N 2.14.

What is claimed is:

1. A compound of the formula:

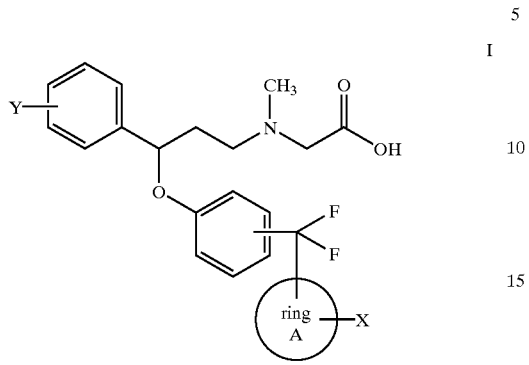

wherein ring A is phenyl, naphthyl, benzothienyl, benzofuranyl, or thienyl; or ring A is a monocyclic aryl or heteroaryl ring containing from zero to four heteroatoms and not containing any adjacent ring oxygen atoms; or ring A is a bicyclic aryl or heteroaryl ring containing from zero to five heteroatoms and not containing any adjacent ring oxygen atoms; and X and Y are each, independently, $(C_1-C_6)$alkyl optionally substituted with from one to seven fluorine atoms; $(C_1-C_6)$alkoxy optionally substituted with from one to seven fluorine atoms, wherein the number of fluorine substituents on the foregoing $(C_1-C_6)$alkyl and $(C_1-C_6)$ alkoxy groups can not exceed the number of positions in such groups that are available for substitution; carboxy; carbo-$(C_1-C_6)$alkoxy; carboxamido; $(C_1-C_6)$alkyl-thio; sulfoxyl; sulfonyl; halo; nitro; cyano; amino; $(C_1-C_6)$ alkylamino and di{$(C_1-C_6)$ alkyl}amino;

or a pharmaceutically acceptable salt thereof.

2. The compound according to claim 1, wherein ring A is selected from phenyl, naphthyl and benzothienyl.

3. The compound according to claim 2, wherein Y is selected from fluoro, bromo, chloro, methyl, ethyl, methoxy, ethoxy, phenyl, benzyl, and acetyl.

4. The compound according to claim 1, wherein X is 4-trifluoromethyl, 4-methyl, methoxy, phenyl, benzyl, or 4-chloro.

5. The compound according to claim 1 having the formula:

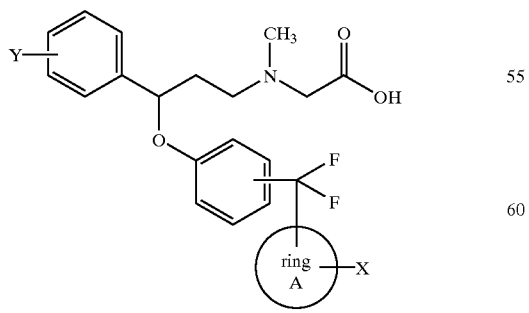

or a pharmaceutically acceptable salt thereof.

6. A compound having the formula:

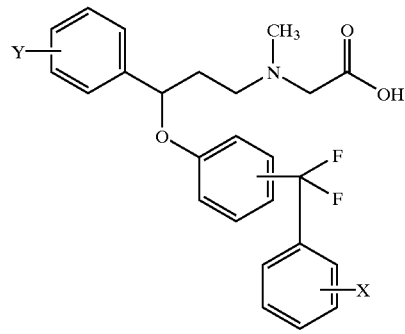

wherein X and Y are each, independently, $(C_1-C_6)$alkyl optionally substituted with from one to seven fluorine atoms; $(C_1-C_6)$alkoxy optionally substituted with from one to seven fluorine atoms, wherein the number of fluorine substituents on the foregoing $(C_1-C_6)$alkyl and $(C_1-C_6)$ alkoxy groups can not exceed the number of positions in such groups that are available for substitution; carboxy; carbo-$(C_1-C_6)$alkoxy; carboxamido; $(C_1-C_6)$alkyl-thio; sulfoxyl; sulfonyl; halo; nitro; cyano; amino; $(C_1-C_6)$ alkylamino and di[$(C_1-C_6)$ alkyl]amino;

or a pharmaceutically acceptable salt thereof.

7. The compound according to claim 6, wherein X is selected from 2-fluoro, 4-fluoro, 4-chloro, trifluoromethyl, acetyl, 2-methyl, 4-methyl, 4-methoxy, phenyl, phenoxy, naphthyl and benzothienyl.

8. The compound according to claim 6, wherein Y is selected from hydrogen, fluoro, chloro, methyl, and methoxy.

9. The compound according to claim 6

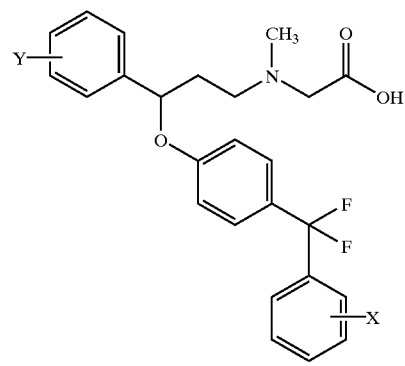

or a pharmaceutically acceptable salt thereof.

10. A compound having the formula:

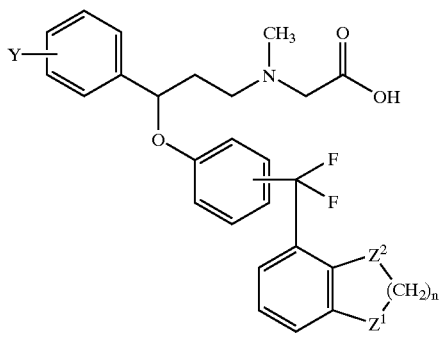

IA wherein Y is $(C_1-C_6)$alkyl optionally substituted with from one to seven fluorine atoms; $(C_1-C_6)$alkoxy optionally substituted with from one to seven fluorine atoms, wherein the number of fluorine substituents on the foregoing $(C_1-C_6)$alkyl and $(C_1-C_6)$ alkoxy groups can not exceed the number of positions in such groups that are available for substitution; carboxy; carbo-$(C_1-C_6)$alkoxy; carboxamido; $(C_1-C_6)$alkyl-thio; sulfoxyl; sulfonyl; halo; nitro; cyano; amino; $(C_1-C_6)$ alkylamino and di{$(C_1-C_6)$alkyl}amino;

wherein $Z_1$ and $Z_2$ are independently selected from O, NH, N-$(C_1-C_5$ alkyl), and S; and n is an integer from 1 to about 3;

or a pharmaceutically acceptable salt thereof.

11. The compound according to claim 10, wherein Y is selected from hydrogen, 2-fluoro, 4-trifluoromethyl, 4-fluoro, 4-chloro, 2-methyl, 4-methyl, 4-methoxy, naphthyl and benzothienyl.

12. The compound according to claim 10, wherein $Z_1$ and $Z_2$ are each O; and n is 1 or 2.

13. The compound according to claim 10, wherein $Z_1$ is O; $Z_2$ is $CH_2$; and n is 1 or 2.

14. A method of treating a disorder or condition selected from psychosis, schizophrenia, conduct disorder, disruptive behavior disorder, bipolar disorder, psychotic episodes of anxiety, anxiety associated with psychosis, psychotic mood disorders selected from severe major depressive disorder; mood disorders associated with psychotic disorders selected from acute mania, depression associated with bipolar disorder and mood disorders associated with schizophrenia; behavioral manifestations of mental retardation, conduct disorder and autistic disorder; movement disorders selected from Tourette's syndrome, akinetic-rigid syndrome, movement disorders associated with Parkinson's disease, tardive dyskinesia, and other drug-induced and neurodegeneration-based dyskinesias; attention deficit hyperactivity disorder; cognitive disorders selected from dementias, age-related dementia and senile dementia of the Alzheimer's type; and memory disorders in a mammal, comprising administering to a mammal in need of such treatment an amount of a compound of according to claim 1 that is effective in treating such condition or disorder.

15. A pharmaceutical composition for treating a disorder or condition selected from psychosis, schizophrenia, conduct disorder, disruptive behavior disorder, bipolar disorder, psychotic episodes of anxiety, anxiety associated with psychosis, psychotic mood disorders selected from severe major depressive disorder; mood disorders associated with psychotic disorders selected from acute mania and depression associated with bipolar disorder, and mood disorders associated with schizophrenia; behavioral manifestations of mental retardation, conduct disorder and autistic disorder; movement disorders selected from Tourette's syndrome, akinetic-rigid syndrome, movement disorders associated with Parkinson's disease, tardive dyskinesia and other drug-induced and neurodegeneration-based dyskinesias; attention deficit hyperactivity disorder; cognitive disorders selected from dementias, age-related dementia and senile dementia of the Alzheimer's type; and memory disorders in a mammal, comprising an amount of a compound according to claim 1 that is effective in treating such disorder or condition.

16. A method of treating a disorder or condition selected from psychosis, schizophrenia, conduct disorder, disruptive behavior disorder, bipolar disorder, psychotic episodes of anxiety, anxiety associated with psychosis, psychotic mood disorders selected from severe major depressive disorder; mood disorders associated with psychotic disorders selected from acute mania and depression associated with bipolar disorder, and mood disorders associated with schizophrenia; behavioral manifestations of mental retardation, conduct disorder and autistic disorder; movement disorders selected from Tourette's syndrome, akinetic-rigid syndrome, and movement disorders associated with Parkinson's disease, tardive dyskinesia, and other drug-induced and neurodegeneration-based dyskinesias; attention deficit hyperactivity disorder; cognitive disorders selected from dementias, age-related dementia, and senile dementia of the Alzheimer's type; and memory disorders in a mammal, including a human, comprising administering to a mammal in need of such treatment a glycine transport inhibiting amount of a compound according to claim 1.

17. A pharmaceutical composition for treating a disorder or condition selected from psychosis, schizophrenia, conduct disorder, disruptive behavior disorder, bipolar disorder, psychotic episodes of anxiety, anxiety associated with psychosis, psychotic mood disorders selected from severe major depressive disorder; mood disorders associated with psychotic disorders selected from acute mania and depression associated with bipolar disorder, and mood disorders associated with schizophrenia; behavioral manifestations of mental retardation, conduct disorder and autistic disorder; movement disorders selected from Tourette's syndrome, akinetic-rigid syndrome, movement disorders associated with Parkinson's disease, tardive dyskinesia and other drug-induced and neurodegeneration-based dyskinesias; attention deficit hyperactivity disorder; cognitive disorders selected from dementias, age-related dementia and senile dementia of the Alzheimer's type; and memory disorders in a mammal, including a human, comprising a glycine transport-inhibiting amount of a compound according to claim 1.

* * * * *